(12) United States Patent
Cooper

(10) Patent No.: US 11,494,571 B2
(45) Date of Patent: Nov. 8, 2022

(54) COMPUTER VISION METHOD FOR IMPROVED AUTOMATED IMAGE CAPTURE AND ANALYSIS OF RAPID DIAGNOSTIC TEST DEVICES

(71) Applicant: Donald Channing Cooper, Boulder, CO (US)

(72) Inventor: Donald Channing Cooper, Boulder, CO (US)

(*) Notice: Subject to any disclaimer, the term of this patent is extended or adjusted under 35 U.S.C. 154(b) by 0 days.

(21) Appl. No.: 17/381,063

(22) Filed: Jul. 20, 2021

(65) Prior Publication Data
US 2022/0027587 A1   Jan. 27, 2022

Related U.S. Application Data

(60) Provisional application No. 63/055,275, filed on Jul. 22, 2020.

(51) Int. Cl.
| | |
|---|---|
| *G06K 7/10* | (2006.01) |
| *G01N 33/543* | (2006.01) |
| *G06K 7/14* | (2006.01) |
| *G16H 30/40* | (2018.01) |
| *G06V 20/10* | (2022.01) |

(52) U.S. Cl.
CPC ... *G06K 7/10722* (2013.01); *G01N 33/54387* (2021.08); *G06K 7/1417* (2013.01); *G06V 20/10* (2022.01)

(58) Field of Classification Search
CPC ............ G06K 7/10722; G06K 7/1417; G01N 33/54387; G16H 30/40
USPC ................................................... 235/462.11
See application file for complete search history.

(56) References Cited

U.S. PATENT DOCUMENTS

| | | |
|---|---|---|
| 9,260,750 B2 | 2/2016 | Hillebrand |
| 10,815,539 B1 | 4/2020 | Brambati |
| 2015/0371613 A1 | 12/2015 | Patel et al. |
| 2019/0128813 A1 | 5/2019 | Clark et al. |
| 2020/0110024 A1 | 4/2020 | Cooper |

*Primary Examiner* — Toan C Ly
(74) *Attorney, Agent, or Firm* — Kenneth Altshuler

(57) ABSTRACT

The disclosed embodiments are generally directed to improving feature detection of rapidly acquired images using camera-enabled mobile devices involving a 2-D decal code, such as a QR code, for improving the reading accuracy of a rapid diagnostic antigen or antibody or enzymatic colorimetric directed test, such as for COVID-19 diagnosis. One primary issue with evaluating a Covid-19 rapid test is detecting and quantifying positive test lines from sampled test strips based on digital images of the test strip. Aspects of the present invention contemplate masking a QR code to improve the sample image resolution and contrast. Other aspects of the present invention contemplate methods and techniques to evaluate a test line on the sample image by enhancing an intensity curve along the test line and control line containing area by way of calculating the instantaneous change in pixel intensity and evaluating the position and intensity of those signals.

20 Claims, 16 Drawing Sheets

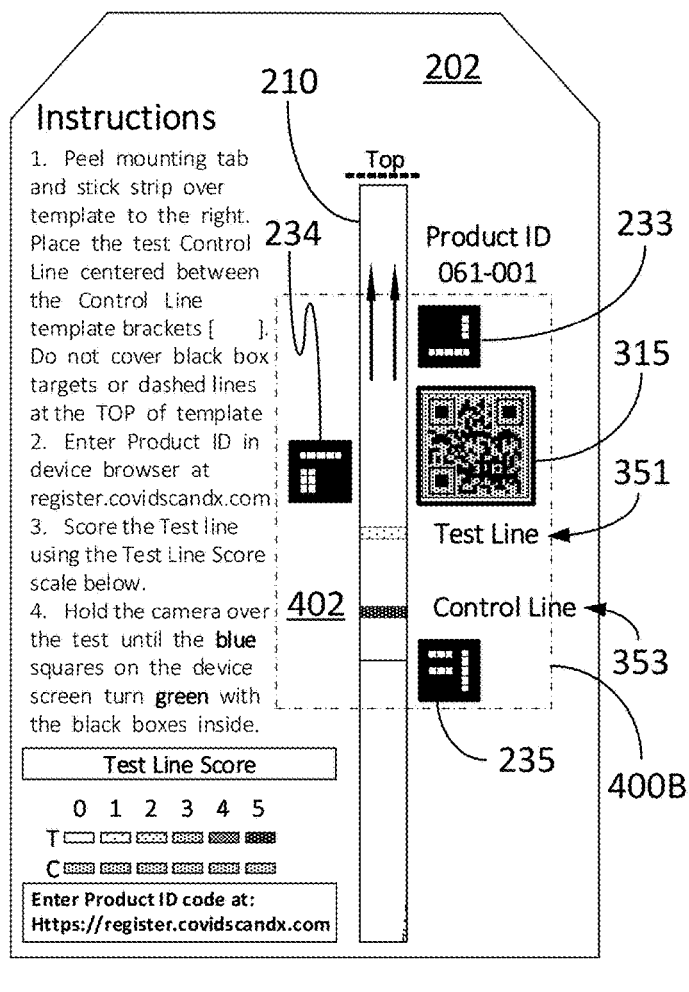
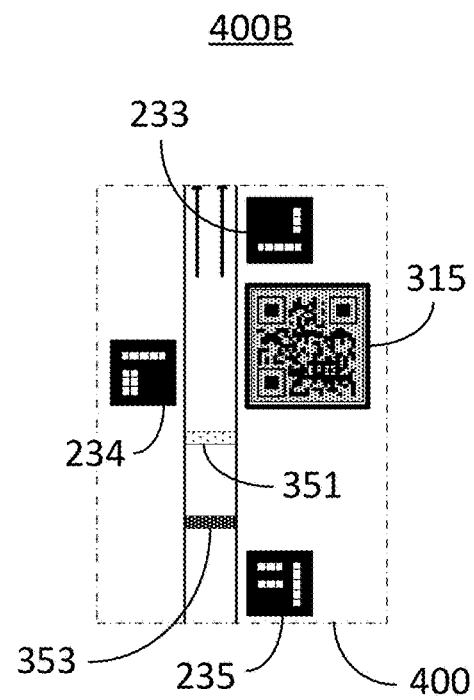
FIG. 7C  FIG. 7D

COMPUTER VISION METHOD FOR IMPROVED AUTOMATED IMAGE CAPTURE AND ANALYSIS OF RAPID DIAGNOSTIC TEST DEVICES

CROSS-REFERENCE TO RELATED APPLICATIONS

This U.S. Patent Application claims priority to and the benefit of U.S. provisional Patent Application No. 63/055,275 entitled COMPUTER VISION METHOD FOR IMPROVED AUTOMATED IMAGE CAPTURE AND ANALYSIS OF RAPID DIAGNOSTIC TEST DEVICES, filed on Jul. 22, 2020.

FIELD OF THE INVENTION

The present embodiments are directed generally to image capture systems where obscuring a Quick Response Code with a mask to improve resolution and/or contrast of an image during image acquisition is accomplished using camera-enabled mobile devices or computers.

DESCRIPTION OF RELATED ART

It is to innovations related to this subject matter that the claimed invention is generally directed.

The year 2020 is distinguished as the year of the Covid-19 pandemic, affecting every corner of the globe. The stunning efficiency in infection rate of this airborne virus is forcing humankind to alter otherwise normal behavior. Covid-19 causes long-term organ damage and death in a frightening number of infected people the likes of which the world has not seen in generations. Fear of this disease is halting movement across borders, stalling economies throughout the world, and changing the way humankind interacts with one another. In an effort to gain some control over the wildfire spread of the corona virus, SARS-CoV-2, the FDA, has fast-traced the development of new emergency use SARS-CoV-2 rapid diagnostic tests that can give a positive, negative result in 30-60 minutes at the point-of-care or at home. One major obstacle to FDA approval is the lack of simple to use rapid tests where the results can be quantified and interpreted with a high degree of sensitivity.

It is to innovations related to the automated image-based detection and quantification of rapid diagnostic tests, such as for SARS-CoV-2 viral antigen and immunoglobulin antibodies, that embodiments of the present invention are generally directed.

SUMMARY OF THE INVENTION

The present embodiments are directed to improving the sensitivity and accuracy of rapid biological tests that may be combined with a QR code as a means for automatically capturing an image of an active biological test sample by effectively reducing the contrast of the QR code, thus obscuring the QR code to the camera while still allowing the QR code information to be processed by the device.

Certain embodiments of the present invention contemplate an immunodiagnostic test strip method comprising: providing a test strip possessing a test line region, a template adjoining/accompanying the test strip, a QR code visibly disposed on the template; exposing the test line region to an activation agent, such as a component of an inactivated viral pathogen or immunoglobin; after the exposing step, focusing a digital camera on the QR code, the digital camera linked to a computer that includes a microprocessor and non-transient memory; partially obscuring the QR code with a contrast reducing mask, and capturing at least one image of the test line region after the exposing step while the QR code is being partially obscured.

Yet other certain embodiments of the present invention envision a method for a test strip evaluation method comprising: providing a smart phone that includes a digital camera, a QR code identification algorithm, and a QR code obscuring mask;-locating a QR code with the camera; creating an obscured QR code with an obscuring mask; focusing the camera on the obscured QR code by way of the QR code identification algorithm; and taking a photograph with the digital camera of the obscured QR code and an unobstructed region extending beyond the obscured QR code.

While other certain embodiments of the present invention imagine a mobile touchscreen computing device comprising: a touchscreen; a digital camera; non-transitory memory; a computer processor; a QR code detection algorithm that locates a QR code displayed on a planar surface, focuses the digital camera on the QR code, acquires an image of the QR code with at least a region extending beyond the QR code with the digital camera, the region including a biologically activated test line region; a QR code obscuring algorithm that partially inhibits (masks) only the QR code, but not the region to the QR code detection algorithm, the QR code obscuring algorithm reduces efficacy of the QR code detection algorithm.

BRIEF DESCRIPTION OF THE DRAWINGS

FIGS. 7A-7D are line drawings of an example of a sample image without a mask and with a mask consistent with embodiments of the present invention;

DETAILED DESCRIPTION

Figure 1A:
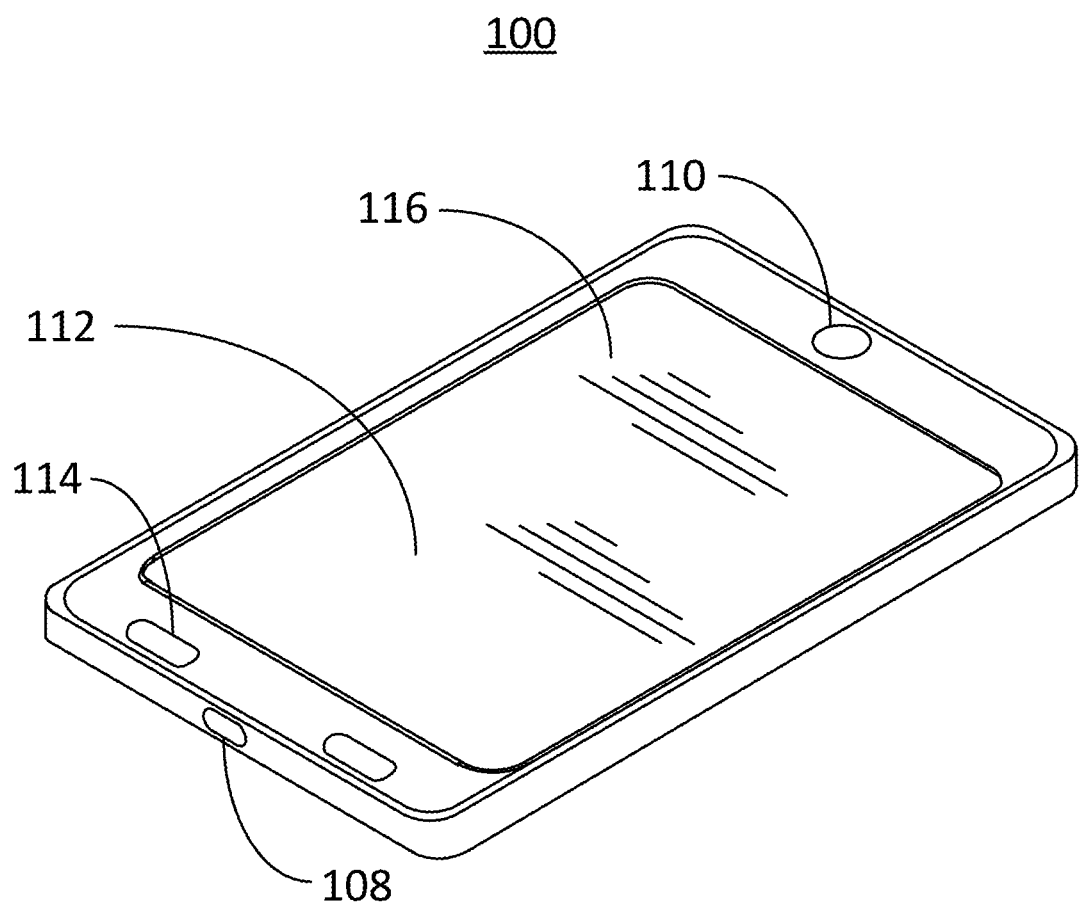
FIGS. 1A and 1B are line drawings of a mobile touchscreen computing device embodiment consistent with embodiments of the present invention.

Initially, this disclosure is by way of example only, not by limitation. Thus, although the instrumentalities described herein are for the convenience of explanation, shown and described with respect to exemplary embodiments, it will be appreciated that the principles herein may be applied equally in other similar configurations involving masking a QR code to improve the picture quality of the surrounding area. The phrases "in one embodiment", "according to one embodiment", and the like generally mean the particular feature, structure, or characteristic following the phrase is included in at least one embodiment of the present invention, and may be included in more than one embodiment of the present invention. Importantly, such phases do not necessarily refer to the same embodiment. If the specification states a component or feature "may", "can", "could", or "might" be included or have a characteristic, that particular component or feature is not required to be included or have the characteristic. As used herein, the terms "having", "have", "including" and "include" are considered open language and are synonymous with the term "comprising". Furthermore, as used herein, the term "essentially" is meant to stress that a characteristic of something is to be interpreted within acceptable margins of the normal world and is analogous with "more or less."

For example, essentially flat, essentially straight, essentially on time, etc. all indicate that these characteristics are not capable of being perfect within the sense of their limits. Accordingly, if there is no specific +/− value assigned to "essentially", then assume essentially means to be within +/−2.5% of exact. In what follows, similar or identical structures may be identified using identical callouts.

Embodiments disclosed herein are generally directed to improving rapidly acquired images involving a 2-D decal code, such as a QR code, with certain particular benefit for improving the reading accuracy of a rapid biological test, such as for SARS-CoV-2. Though tests can range from detecting various chemicals to particular biological/genetic materials, many such tests provide nebulous results especially when the corresponding test samples include only a small amount of material. With regards to SARS-CoV-2, one downfall with present testing is the number of false negative results, or simply 'false negatives'. As of today, of the people that are actually sick with Covid-19, 25% are sent home and into the public mistakenly because of a false negative Covid-19 test. Clearly, this jeopardizes spreading the disease amongst the greater population because a negatively tested but positively infected person unknowingly may still infect others. One of the challenges in detecting Covid-19 is the often hard to detect a positive test line that appears on a test resulting from infectious viral particles. Certain embodiments of the present invention address a rapid SARS-CoV-2 virus detection test using a cell phone or tablet that photographs a nasal and/or saliva activated test strip by way of an adjacent two-dimensional (2-D) focus decal, such as a QR code, bar code, or other focusing mark located next to the test strip. Certain software programs automatically focus on 2D decal and then snap one or more pictures of the 2D decal and surrounding area, including the test strip. One problem with this method is that the quality of the picture taken of the Covid-19 test line based on focusing on the 2D decal may be too faint or out of focus or in poor lighting for positive test line signal detection. Moreover, the analytics used to detect a faint SARS-CoV-2 test line may not be sophisticated enough to render the test line. Some embodiments described herein employ obscuring a 2-D decal to an automatic focusing software program in order to force the software program to essentially take the best picture with the best contrast possible. Certain other aspects of the present invention envision utilizing a variety of mathematical techniques including calculus and statistics to detect the presence of a positive test result from diagnostic test images.

Figure 1B:
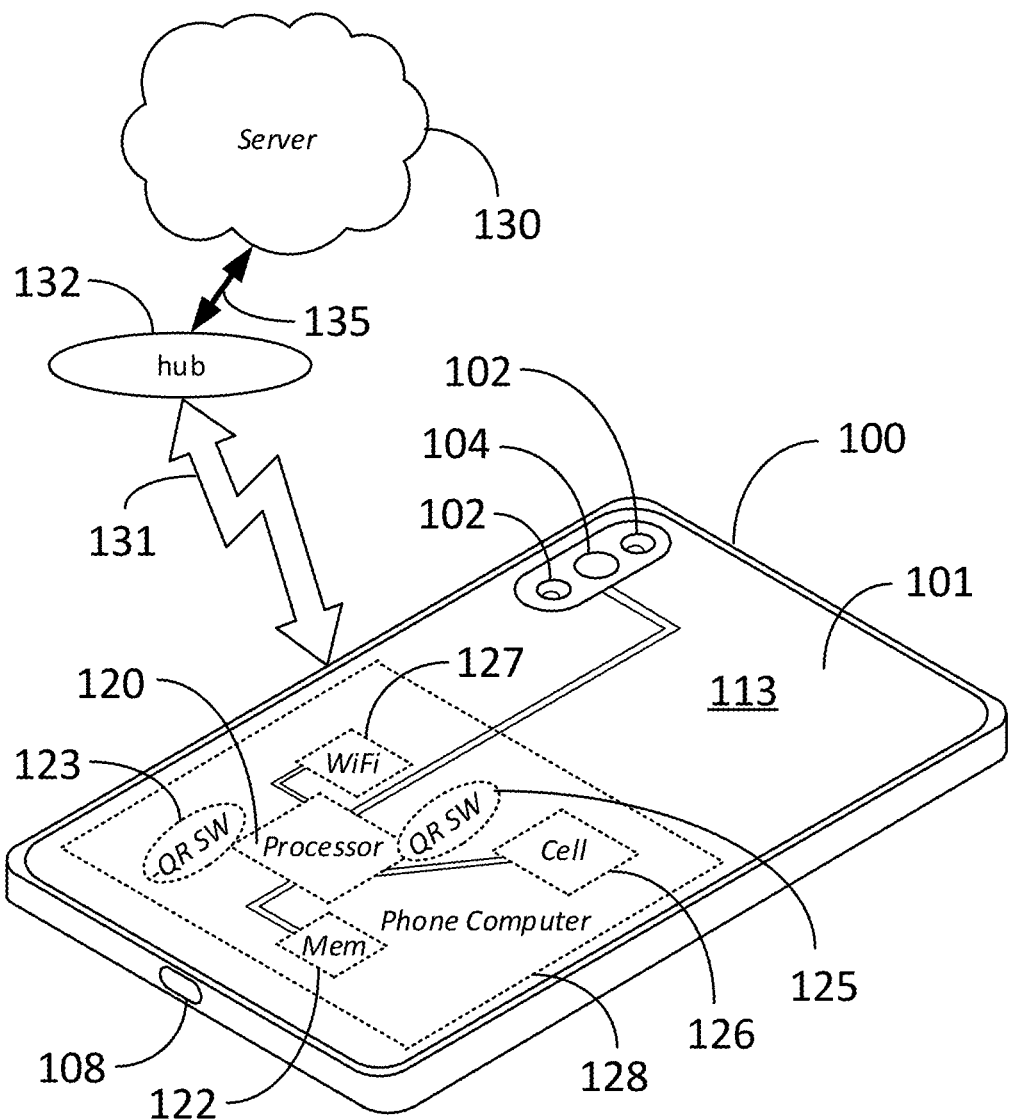

FIGS. 1A and 1B are line drawings of a mobile touchscreen computing device embodiment depicted to provide an environment in which embodiments of the present invention can be advantageously practiced. FIG. 1A is an isometric front surface 112 view of a cell phone 100 showing a touchscreen 116, front camera 110, speakers 114 and a female power receiving port 108. The touchscreen 116 serves as a graphical user interface (GUI) that both displays pictures and can be manipulated through the touch of a human finger. Hence, the touchscreen displays images, whether live or previously taken by the camera 110/102 or elsewhere in addition to displaying text. The touchscreen 116 is one embodiment of a display screen.

FIG. 1B is an isometric back surface 113 view of the cell phone 100 wirelessly communicating with a server 130 consistent with embodiments of the present invention. A touchscreen camera-enabled mobile device is a computerized electronic device that generally has a cellular chip 126 and antenna (not shown) which connects to a cellular tower (not shown). The present cell phone configuration 100 depicts a dual camera system 102 with a central LED illumination source 104 that can be used for a flash. A block diagram of the computer system 128, cellular chip 126, microprocessor 120, and non-transitory memory 122 (such as a solid-state memory card) is shown as dotted lines indicating that the computer system 128 is located within the cell phone case 101. The processor 120 generally functions as the computing engine that controls all aspects and functionality of a touchscreen cell phone 100. For example, a QR code detection algorithm 125 (which can be stored in memory 122 and executed on the processor 120), can be accessed via an end-user (not shown) by opening a QR code capture link via an icon (not shown) displayed on the touchscreen 112. A QR code detection algorithm 125 manipulates the rear-facing camera 102 to locate and focus on a QR code 300 (of FIG. 2). Once located and focused, the camera 102 takes a digital picture of the QR code 300, and sends it to the processor 120, which can transfer it to memory 122 and/or transmit the image to a server 130 via wireless link/hub 132. The hub 132 can be a cellular communications hub, such as a cell tower transceiver that is linked 131 with the cellular chip 126 or a Wi-Fi hub that is linked to the cell phone Wi-Fi device 127, just to name several examples. The hub 132 is connected 135 to a server system 130, which in certain embodiments envisions a cloud service, such as Amazon S3. QR code processing can occur in the server system 130 or optionally locally in the cell phone 100. Shown for reference and discussed later is a QR code obscuring algorithm 123 denoted "-QR SW" to indicate that it works against or otherwise inhibits optimal/near optimal functioning of the QR code detection software 125.

Figure 2:
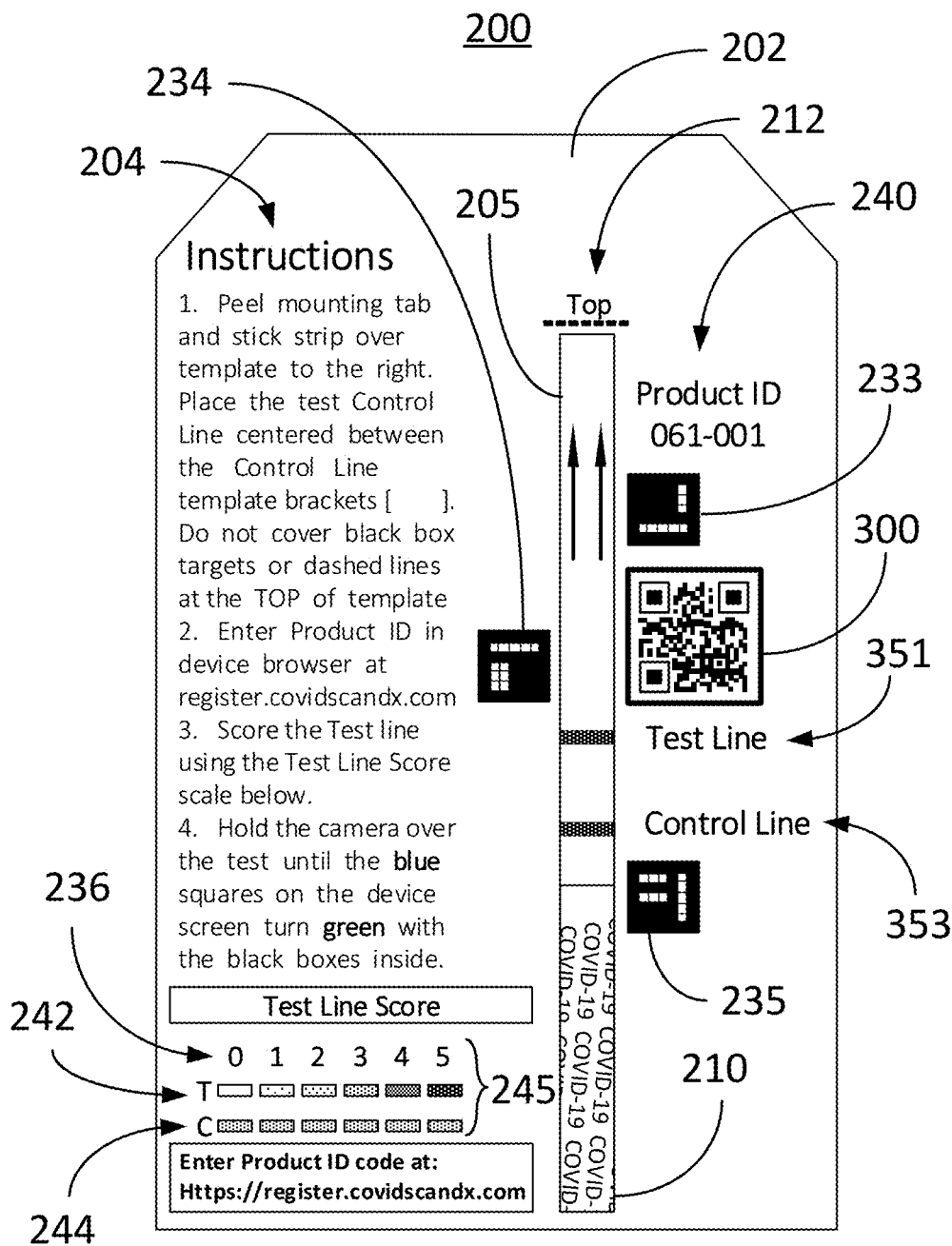
FIG. 2 illustratively depicts a line drawing of a commercial embodiment of a test card template in which embodiments of the present invention can be practiced.

FIG. 2 illustratively depicts a line drawing of a commercial embodiment of a test card template in which embodiments of the present invention can be commercially practiced. The biological test card template 200 (or simply "test card") produced by Neuroganics Diagnostics, LLC. of Northglenn, CO., illustratively shows a biological test strip 210, visibly displayed in the center of the test card 200 next to a QR code 300 and three (Aruco) alignment targets 333, 334 and 335. This test card 200 can be used for procuring a biological sample that is analyzed in a server system 130 but can just as easily be analyzed locally in a cell phone, tablet, or other computing system. The test card 200 presents a variety of informative elements to an end-user. For example, Instructions 204 with steps enumerated 1-4 are printed on the card front surface 202 to the left of the test strip 210. Below the instructions 204 is a map of test-line scores 245 that include different pigmented test rectangles 242 that correspond to six different pigmented test rectangles 242. Each rectangle has different levels of test exposure intensity, ranging from intensity scores 0-5 236, wherein 0 has no intensity and 5 has a maximum intensity. Six pigmented control rectangles 244, that are all the same color and intensity, are aligned with the six different pigmented test rectangles 242 for comparison against the test rectangles 242. To the right of the test strip 210 is a product ID and serial number 240, a QR code 300, test-line 351 and control-line 353 locations. The test strip 210 is adhered to the test card front surface 202 between the top dotted lines 212 and the bottom dotted lines 214. Optionally, the test strip 210 is placed within a window/aperture 205 in the test card 200. Another embodiment envisions the test strip 210 simply integrated with the test card 200.

Figure 3A:
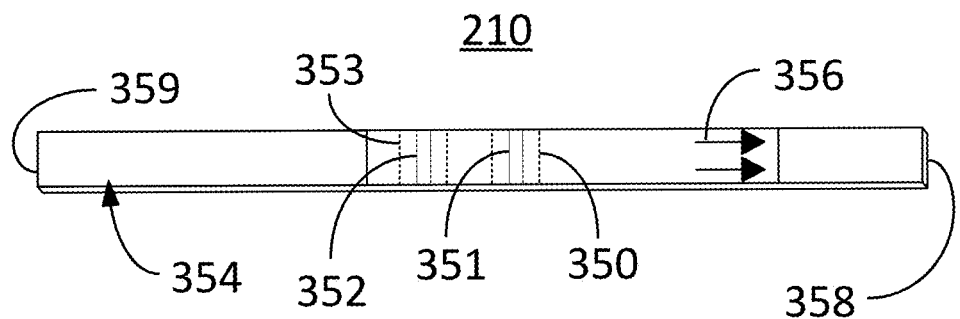
FIGS. 3A and 3B are line drawing depictions of a test strip embodiment with an applied pathogen consistent with embodiments of the present invention.
Figure 3B:
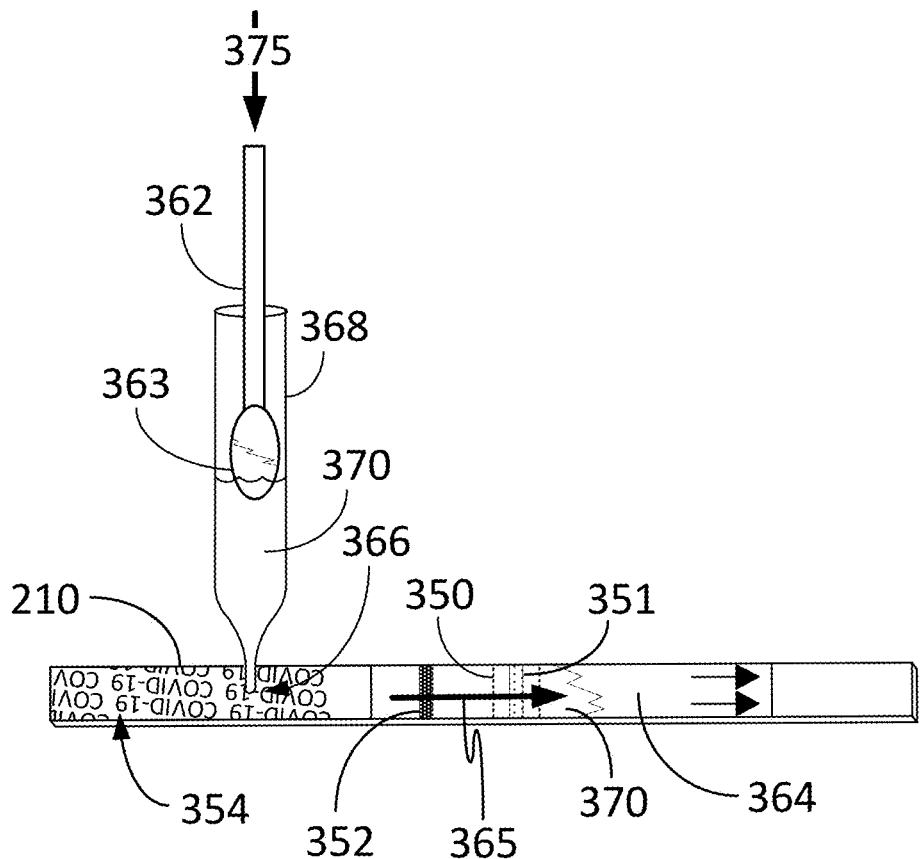

FIGS. 3A-3B are line drawing depictions of a test strip embodiment applied with a pathogen consistent with embodiments of the present invention. FIG. 3A depicts a new and unused SARS-CoV-2 detecting test strip, which is one of many possible commercial examples of an unused test strip 210. The unused test strip 210 has no developed control-line 353 within the control-line region or test-line 351 within the test-line region 350. The dotted lines on either side of the test-line 351 and on either side of the control-line 353 are not necessarily present in the commercial embodiment of the test strip 210. The double arrows 356 point towards the top end 358 of the test strip 210 and a shown for the benefit of the end-user. A Covid-19 label 354 is visibly disposed towards the bottom end 359 of the test strip 210.

FIG. 3B illustratively depicts an example of a nasophyryngeal (nasal and saliva) swab test, NPS, applied to an unused test strip 210 via a pipet 368, or test tube (not shown), as depicted by arrow 375. An end-user collects an NPS sample 363 from their mouth and nostril via a clean swab 362 and then mixes the collected NPS sample 363 (on the swab tip 360) in the sample solution to create a NPS sample and buffer mixture 370. In the present embodiment an unused test strip 210 has no indication of a test-line 351 or a control-line 353; it is simply blank. For example, if the test strip background 364 is white, then the test-line region 350 and the control-line region 352 will also be white. The end-user then applies the NPS sample and buffer mixture 370 via the pipet tip/aperture 366 on an absorbent pad 354 on the test strip 210, which gathers the mixture 370. As shown by arrow 365, the mixture 370 wicks across the membrane of the test strip 210 across the control region 352 and the sample region 350. After approximately 30 minutes the control-line 353 is developed and the test-line 351 barely shows pigmentation (considered a very weak test-line), however it is consistent with a developed line nonetheless.

One commercial embodiment of the Covid-19 test strip 210 produced by Entvantage Diagnostics, Inc., headquarted in Austin, Tex., is one embodiment of a test platform, which can include diagnostic test cartridges, diagnostic test plates, diagnostic test sheets, etc. By way of example, the Covid-19 test strip 210 uses an immunochromatographic assay for rapid detection of SARS-CoV-2 antigen in nasophyryngeal secretions (NPS) samples. The test-line 351 and control-line 353 are generally composed of a nitrocellulose membrane that is sensitized with monoclonal antibodies directed against SARS-CoV and SARS-CoV-2 highly conserved nucleoprotein antigen. A second monoclonal antibody is conjugated to colloidal gold nanoparticles, which is immobilized on the membrane. The NPS are mixed with a lysis buffer 370 when collected by a transport medium, such as by a swab 362. When this mixture 370 comes into contact with the nitrocellulose test-line 351 and control-line 353, the conjugate migrates with the NPS sample mixture 370 by passive diffusion thus coming into contact with anti-SARS NP antibodies adsorbed on to the nitrocellulose lines 351 and 353. Between 15 and 30 minutes after the NPS sample mixture 370 diffuses or is otherwise spread over the test-line 351 and control-line 353, red pigmentation becomes visible in the control-line 353, and for a positive result, a red test-line 351 develops. A positive test-line 351 is indicative of the NPS sample 363 containing SARS-CoV-2, whereby the conjugate viral complex will remain bound to the anti-SARS-CoV-2 antibody immobilized on to the nitrocellulose. If the test is negative, only the red control-line 353 will appear. If the SARS-CoV-2 concentration is low, the test-line 351 may present a subtle or faint red line that is essentially indetectable, or otherwise not detectable by a human eye or normal resolution digital photograph.

One embodiment comprises a combined use of a chemical additive to a liquid buffer 370 with imaging, which includes chemical substance including visible dye, fluorescent chemical dye, drug (which can include dye) or contrast agent. Specifically, the chemical additive is applied, or optionally mixed, to the liquid buffer 370 containing the biological sample 363 in a manner to change detectability by either increasing or decreasing the intensity of the test line 351, control line 353 or background 364 when captured. Use of such an agent may increase or decrease dwell time of the sample interaction with the test binding agents or may increase or decrease the affinity of the sample analyte with test binding agents when mixed with the sample 363 (or buffer 370 with a dissolved sample 363). This provides a useful signal to measure the kinetics of the test kinetics and improve the automated interpretation of a positive, negative or invalid test result.

Chemical additives may also be used as contrast agents to enhance faint signals of the test band 351 or optionally dampen a strongly visible test band 351 or control band 353. The are chemical additives that can be put in a buffer solution that change the properties of the mixture 370 to alter detectability of the test sample material 363, such as a SARS-cov-2 virus, via image capture 400. The chemical additives can be applied to drugs that are ingested prior to nasal or oral sample collection 363 containing ingredients, such as Phenylephrine Hydrochloride (1.0%), Benzalkonium Chloride, Citric Acid, Sodium Chloride, and/or Sodium Citrate. Optional chemical additives can include excipients such as ion chelators, ionic or nonionic surfactants or hydrophilic dyes, like methylene blue or lipophilic dyes nile red. Chemicial additives that can be used to decrease the test signal intensity includes Vicks VapoCool Sore Throat Spray containing benzocaine, menthol, alcohol, D&C Yellow No. 10, FD&C Blue No. 1, glycerin, propylene glycol, saccharin sodium, sucralose. The aforementioned chemical additive examples may be applied prior to sample collection or added afterwards to the collected biological sample 363 or incubated with the immunodiagnostic test buffer in concentrations less than 10% of total volume, or some other concentration demonstrating efficacy such as between 0.1% and 20%. Yet other embodiments consider between 2.5%-7.5% chemical additive being sufficient. The chemical additives may also be used together with image-based analysis and algorithms to increase the overall test sensitivity at the limit of detection or measure the kinetics of reaction.

Figure 4A:
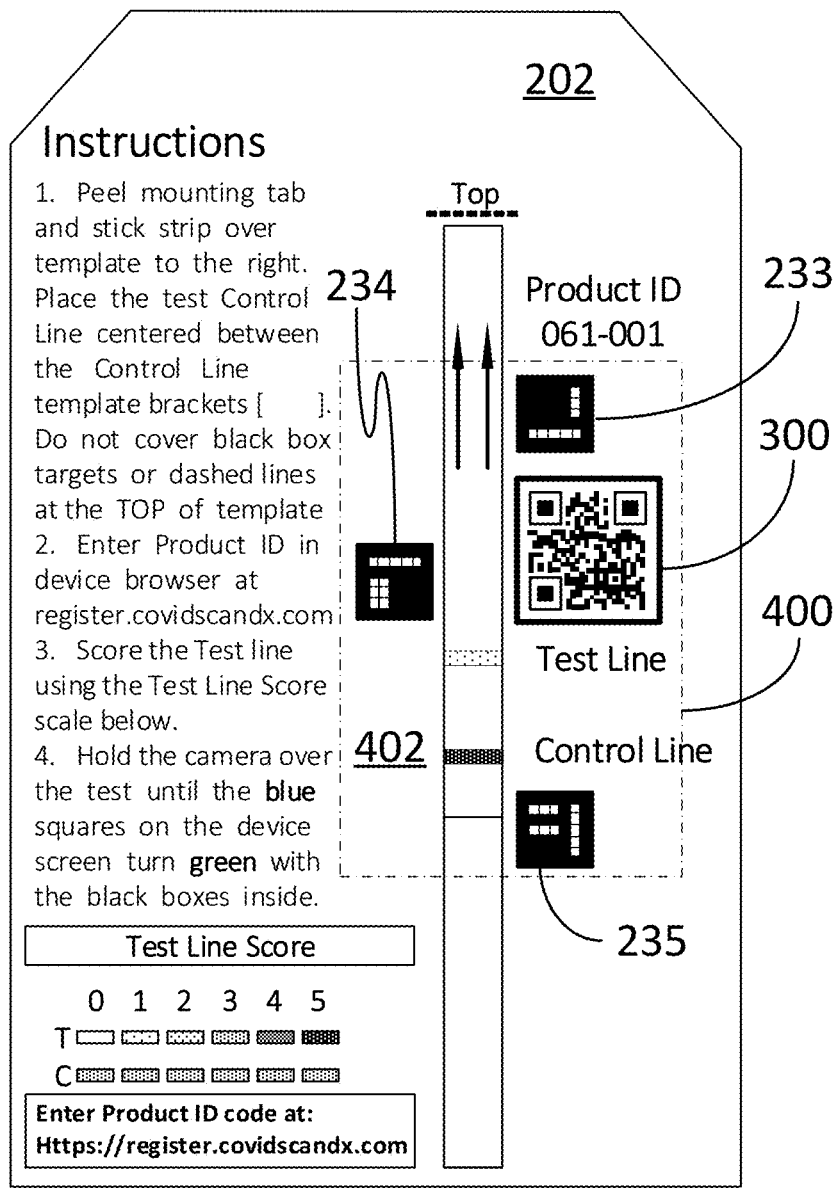
FIG. 4A shows the developed test strip of FIG. 3B accompanied by the test card front surface.

As discussed in conjunction with FIG. 2 the test strip 210 can accompany a test card 200 that possesses a QR code 300 and three Aruco targets 233, 234 and 235 to quickly and automatically transfer test strip image information for analysis to a server 130. FIG. 4A shows the developed test strip 210 of FIG. 3B accompanied by the test card front surface 202. As shown, the test strip 210 possesses a very weak test-line 351. Certain commercial embodiments envision an end-user typing a web address into their internet browser displayed on their smart cell phone 100, which by way of example here is https://register.covidscandx.com. After entering in unique indicia, such as a Product ID 240, a QR code identification algorithm 125 retained in the cloud 130 behind the web address will automatically run on the smart phone processor 120. The QR code identification algorithm 125 operates the rear-facing camera 102 to locate (triangulate over) the QR code 300 and Aruco targets 233, 234 and 235, focus and take at least one picture that includes the QR code 300 and Aruco targets 233, 234 and 235.

Figures 4B, 4C, 4D:
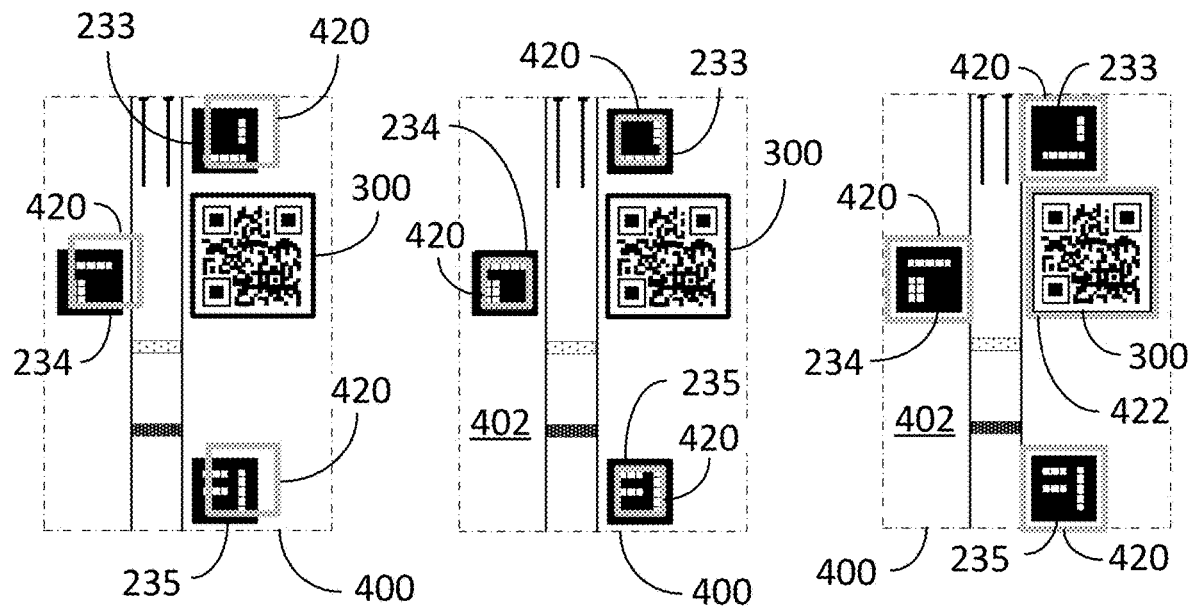
FIGS. 4B-4D illustratively depicts an embodiment showing how a sample images captured consistent with embodiments of the present invention.

FIGS. 4B-4D illustratively depict an example of locating the Aruco targets and QR code to capture a sample image consistent with embodiments of the present invention. One operational example of QR code identification software 125 is by way of Open CV (computer vision) platform, which is a JavaScript open source software that can be made to run by visiting the web URL. Upon entering the website (https://register.covidscandx.com), an end-user will hover the cell phone 100 over the card front surface 202 whereby a live image will be visibly displayed on the touchscreen 116. There are three target points overlaying the image that need to align with the three Aruco targets 233, 234 and 235. When the three target points (not shown) are in close proximity of the three Aruco targets 233, 234 and 235 three Aruco target boxes 420 (depicted as light gray in this figure) will appear in close proximity of the three Aruco targets 233, 234 and 235, FIG. 4B. Close proximity can be within 20% of the Aruco square length or width, or some other value such as less than 50%. Optionally, close proximity can be within a certain distance, such as within a quarter-inch of an Aruco square perimeter, for example. As shown in FIG. 4B, the three Aruco target boxes 420 are approximately the same size as the Aruco targets 233, 234 and 235 but offset. FIG. 4C shows what an end-user would see if they have moved the camera 102 too close to the card front surface 202 because the Aruco target boxes 420 are smaller than the Aruco targets 233, 234 and 235, which would make the picture blurry. FIG. 4D shows the Aruco target boxes 420 essentially framing the Aruco squares 233, 234 and 235 whereby Open CV locks on to the Aruco targets 233, 234 and 235 and the QR code 300 and puts a QR box 422 around the QR code periphery 304 all within a matter of milliseconds before taking one or more pictures. Certain embodiments envision the Aruco target boxes 420 changing colors when they first start locking on to the Aruco squares (for example they can be red) to when the Aruco target boxes 420 are aligned and in-plane ready to take a picture (for example they can turn green). Because the QR code identification software 125 locks on to the Aruco squares 233, 234 and 235 and the QR code the sample image/s 402 will likely not have near optimal lighting, contrast, color and/or focus.

Figure 5A:
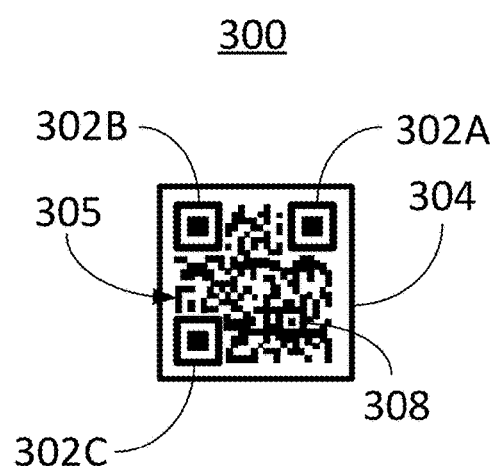
FIG. 5A is a line drawing of a QR code consistent with embodiments of the present invention.

The QR code embodiment of FIG. 5A is a well suited information tag for use with a cell phone or tablet 100 connected to a website as will now be discussed. The QR code 300 is used by way of example to illustrate certain embodiments of the present invention, and is not to be considered limiting in any way because other kinds of like codes, such as optional QR code configurations, bar codes, etc., can be equally used without departing from the scope and spirit of the present invention. The present QR code 300 is a type of two-dimensional matrix barcode that is a machine-readable optical label containing information about the test card 200. More specifically, as shown the QR code 300 comprises three position patterns/boxes 302A, 302B and 302C that are framed squares in three corners with a smaller frame square 308 used for alignment. The required pattern 305 includes unique data written in the QR code about the test card 200 in addition to timing, and potential error code correction information. With reference to the cell phone 100, QR code identification software 125 that is retained in memory 122 can be accessed and executed by the processor 122 to locate the QR code 300, focus the camera 102 on the positioning patterns/boxes 302 and on the alignment pattern 308 of the QR code 300. Because of the binary nature of the QR code 300, the camera 102 need only focus with enough resolution to capture an understandable QR code image. Accordingly, a QR code algorithm 125 quickly locates the QR code, typically within 200 ms, and captures one or more images of the QR code 300 storing it to memory 102 or sending it to a remote computing system, such as a server 130.

Figure 5B:
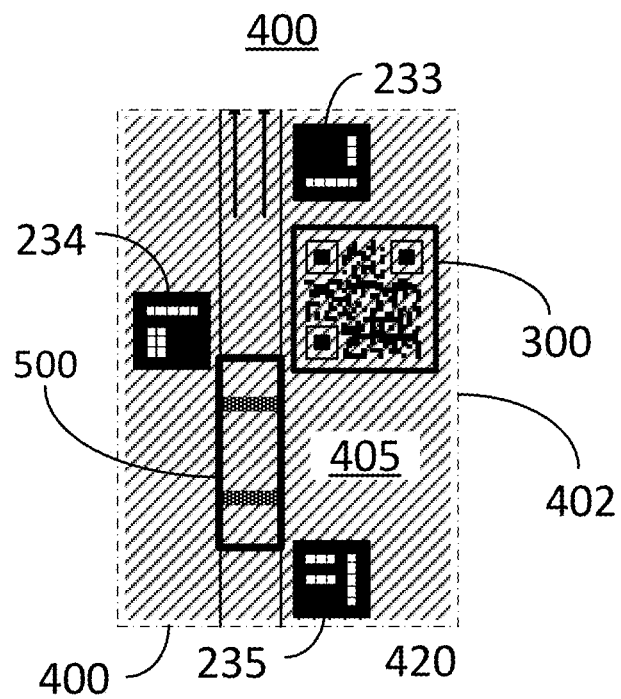
FIG. 5B shows one embodiment of a sample image taken that includes the QR code consistent with embodiments of the present invention.

FIG. 5B shows one embodiment of a sample image 400 taken that includes the QR code 300 and the Aruco targets 233, 234 and 235. With reference to the test card 200, after the QR code algorithm 125 locates the QR code 300 and the Aruco targets 233, 234 and 235, the camera 102 captures a sample image 400 that includes the QR code 300 and surrounding region 405. As shown, the sample image 400 is defined by an image perimeter 402 that extends beyond the QR code 300 to include a test window 500 that comprises the test-line region 350 in the control-line region 352. The test window 500 is defined in two dimensions by the Aruco targets 233, 234 and 235. In the present embodiment the image perimeter 405 is essentially defined by the limits of the Aruco targets 233, 234 and 235 and the QR code 300. Certain other embodiments envision the image perimeter 402 extending a predefined distance beyond the closest edge of the Aruco targets 233, 234 and 235 and the QR code periphery 304.

In certain embodiments, 5 images defined within the image perimeter 402 are automatically taken within 1 second and sent to the cloud server 130. Because the QR code identification algorithm 125 is configured to locate, focus, and take one or more images very quickly (for example, in 200 ms), the resolution of the test-line region 350 may be insufficient to identify a positive test-line 351. Poor resolution of a test-line 351 is a leading cause for a false-negative result. With this in mind, certain embodiments of the present invention envision partially obscuring the QR code 300 to force the QR code identification algorithm 125 to better focus and improve resolution and/or exposure time of the test-line region to reduce the number of false-negative results.

Figure 6A:
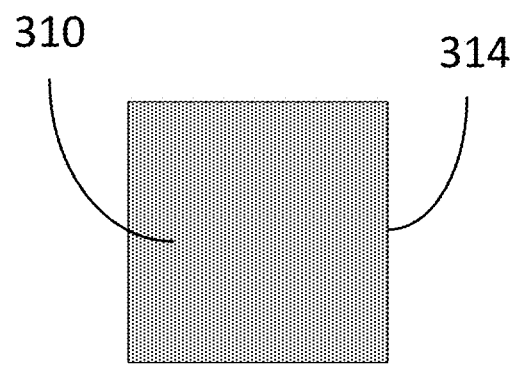
FIGS. 6A-6C illustratively depict a QR code identification algorithm obscuring mask consistent with embodiments of the present invention.
Figure 6B:
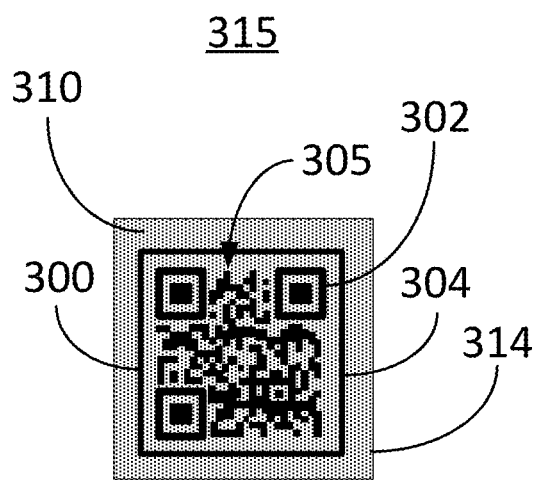
Figure 6C:
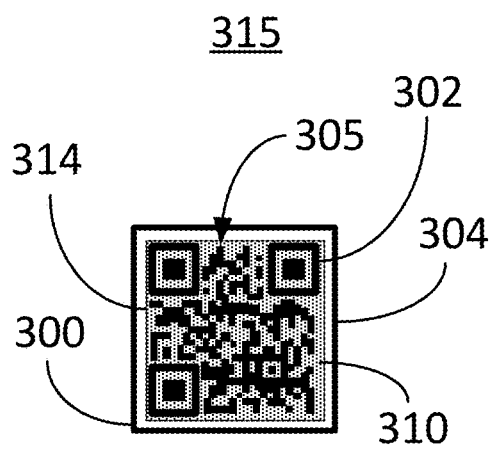

FIGS. 6A-6C illustratively depict a QR code identification algorithm obscuring mask consistent with embodiments of the present invention. FIG. 6A shows only a mask 310, which is configured to partially obscure identifying the QR code 300 via the QR code identification algorithm 125. In the present embodiment, the mask 310 is a shaded square defined by a mask perimeter 314, however any other two-dimensional shapes can be utilized without departing from the scope and spirit of the present invention. In addition, though the mask 310 is a shaded region, this is for purposes of illustration wherein obscuring the QR code 300 can also be accomplished by blurring, filtering a particular color, or some other technique to reduce the QR code identification algorithm's efficacy. FIG. 6B depicts the mask 310 obscuring the QR code 300, which is collectively referred to as the masked QR code 315. As shown, the mask 310 overlays the QR code 300 with the mask perimeter 314 extending beyond the QR code perimeter 304. FIG. 6C depicts a masked QR code 315 with the mask 310 overlaying the QR code 300 wherein the mask perimeter 314 is within the QR code perimeter 304. The mask 310 still obscures the three positioning boxes 302 and required pattern 305 as viewed by the QR code identification algorithm 125. Certain embodiments of the QR code mask 310 envision a QR code obscuring algorithm 123 that starts running when the QR code identification algorithm 125 starts running. Accordingly, in this embodiment the QR code obscuring algorithm 123 may darken, overly lighten, blur, reduce contrast, or obscure the QR code 300 some other way. This forces the QR code identification algorithm 125 to slow down, sharpen focus, improve contrast, lighting, etc., simply to obtain an image of the QR code 300 (sometimes at or near the limits of what the QR code identification algorithm 125 is able to take before timing out from failure to see the QR code 300 adequately). The QR code obscuring algorithm 123 intentionally hinders, reduces, or otherwise inhibits the functionality of the QR code identification algorithm 125 from clearly and easily seeing the QR code 300. In this way, the quality of an image captured of the test window 500 and more specifically the test-line 351 is improved, if not merely optimized to reduce false-negative test results.

Figure 7A:
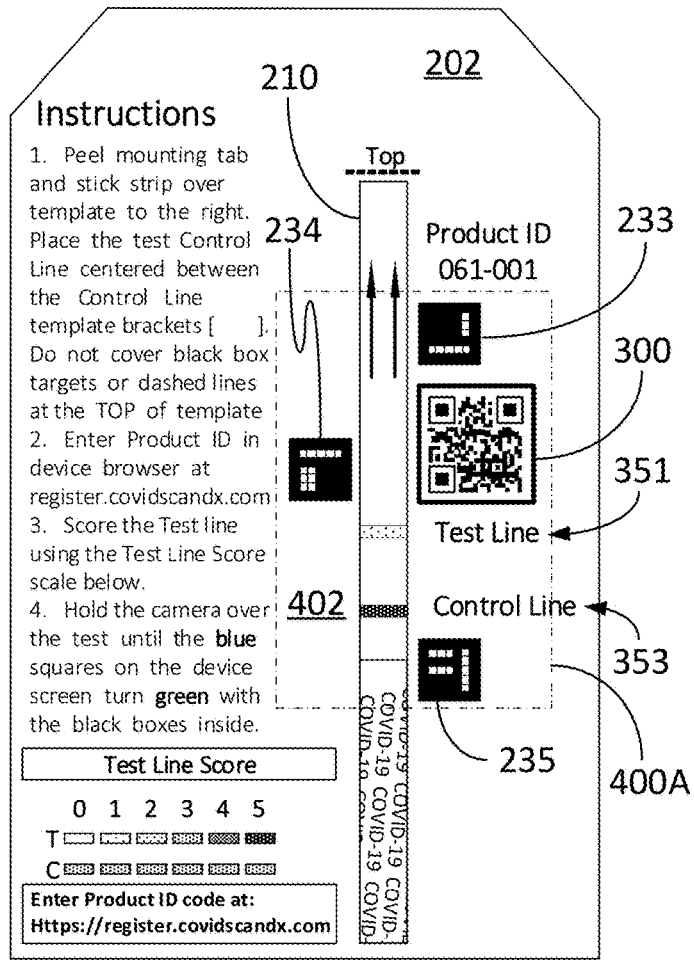
Figure 7B:
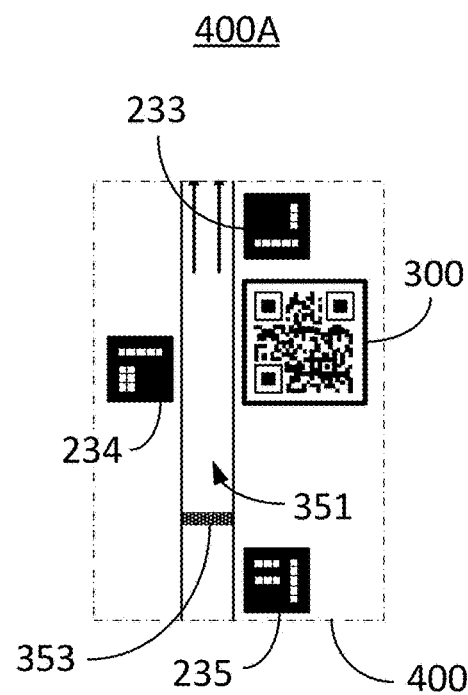

FIGS. 7A-7D are line drawings of a sample image without a mask and with a mask consistent with embodiments of the present invention. FIG. 7A depicts a developed test strip 210 wherein the test-line 351 barely shows pigmentation. A specimen image 400A is taken of the Aruco targets 233, 234 and 235, the unmasked QR code 300, the test-line 351 and the control-line 353. As shown in FIG. 7B, the sample image 400A definitively shows a control-line 353 but shows no test-line 351 because the resolution and/or contrast is inadequate to definitively show the test-line 351. FIG. 7C depicts the developed test strip of FIG. 7A, wherein the test-line 351 barely shows pigmentation, but this time a specimen image 400C is taken of the masked QR code 315 along with the test-line 351 and control-line 353 (and Aruco targets 233, 234 and 235). As shown in FIG. 7D, the sample image 400C definitively shows the control-line 353 in addition to the test-line 351 because the overlaid mask 310 forced the QR code capturing algorithm 125 to take a higher resolution image within the image perimeter 402 as compared with the unmasked image 400B.

Figure 8A:
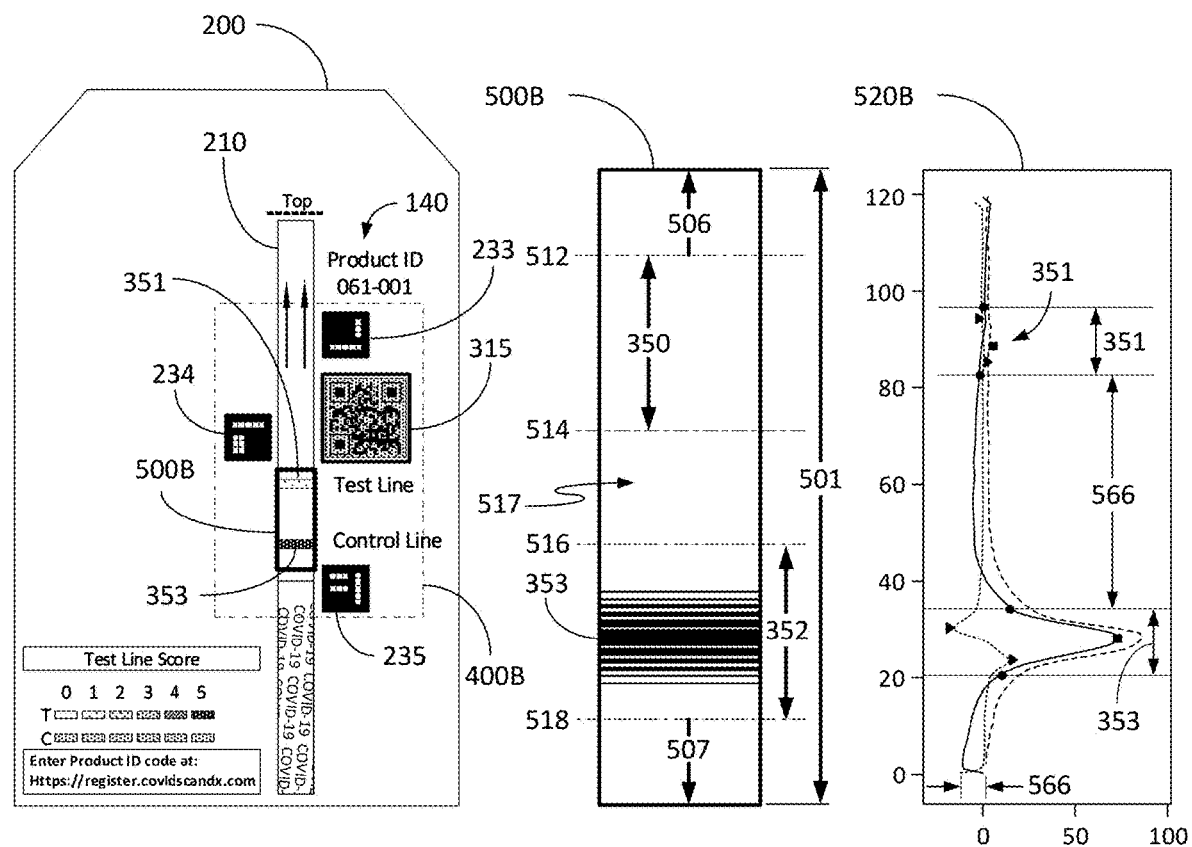
FIGS. 8A-8C illustratively depict evaluating the presence of an otherwise nebulous test-line consistent with embodiments of the present invention.
Figure 8B:
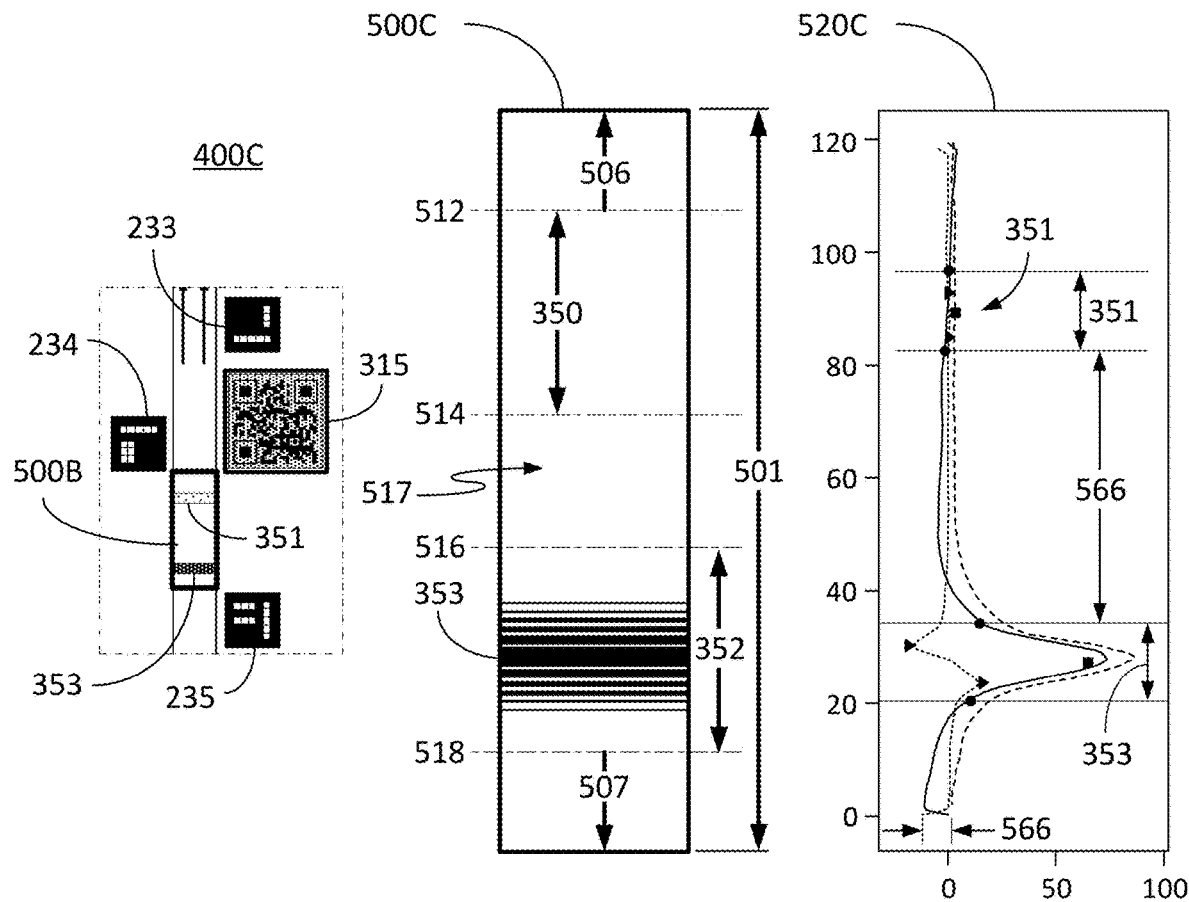
Figure 8C:
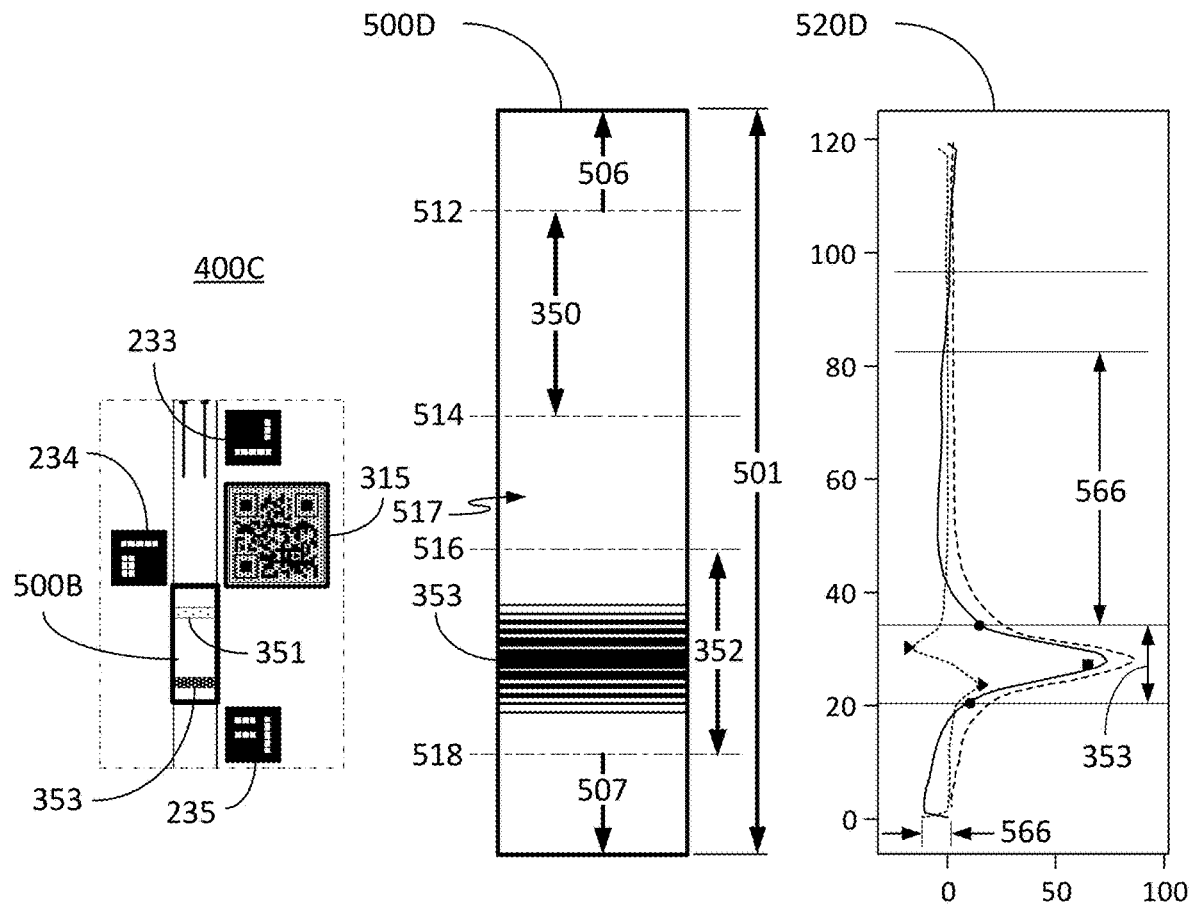
Figure 9:
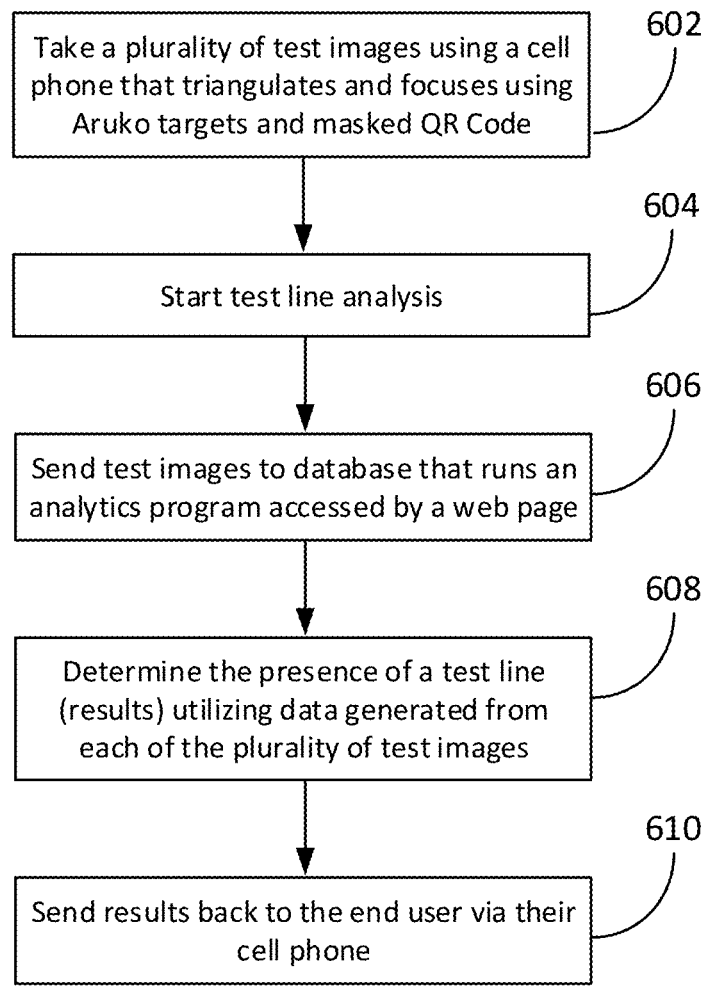
FIG. 9 is a block diagram of a method embodiment showing steps to analyze data consistent with embodiments of the present invention.

FIGS. 8A-8C illustratively depict evaluating the presence of an otherwise nebulous test-line consistent with embodiments of the present invention. FIGS. 8A-8C are described in view of the steps shown in the method block diagram of FIG. 9. After taking a plurality of sample images 400 of a masked QR code 315 (which in this example is three sample images 400B, 400C and 400D) and test window 500 and then sending the sample images 400 to the cloud 130 along with the sample card ID 175, step 602, analysis of the sample images 400 for the presence of a positive test-line 350 commences, step 604. FIG. 8A shows the test card 200 with a first sample image 400B of the masked QR code 315 and the corresponding the first test window 500B, which frames the control-line 353 and test-line 351 displayed on the test strip 210. The first test window 500B illustratively shows that the test region 350, between boundary lines 512 and 514, which is essentially blank because any test-line in the test-line region 350, is so weak that it is extremely difficult to see with the naked eye. The test window 500 extends above the test region 350, shown by an upper arrow 506, below the control-line region 352, shown by the lower arrow 507. The control boundary lines 516 and 518 define the control-line region 352. The lengths 506 and 507 can be different. The test line 351 and the control line 353 are separated by a known separation distance 566, which in certain embodiments is approximately 9 mm.

An analytics program/algorithm, which can be operated in the cloud 130, is run to look at each of the sample images 400B, 400C and 400D, step 606. An example of an analysis is depicted in the far right test-line probability chart of FIG. 8A. More specifically, the first test-line probability chart 520B, to the right of the first test window 500B, comprises three different curves (560, 562 and 564) associated with pigmentation along the test window length 501. The dashed line curve is a raw image curve 560 of any pigmentation along the test window length 501. Because the raw image curve 560 floats off axis due to background noise, such as shading along the test window length 501, a normalized curve 562, which is a subtracted curve shown by the solid line, subtracts the background noise. The dotted line curve is an intensity derivative curve 564, plotting the slope of a change of intensity over the test window length 501, di/dl. The intensity derivation curve 564 serves to magnify subtle changes in intensity along the test window length 501. As shown in the first test-line probability chart 520B a) the solid circle markers show the predicted test line and control line widths based on the normalized curve 562, b) the solid square markers show the measured peak of the test line 351 and control line 353 based on the normalized curve 562, and c) the solid triangle markers show the maximum slope changes of the derivative curve 564. Mathematical manipulation of the curves can be utilized to assist in determining the presence of a test line 351. For example, the test line amplitude can be compared with the noise ratio of the signal, the amplitude control peak, relative peak locations and distances, and area under the curves (integration), just to name several mathematical comparisons to assist in determining the presence of a test line.

FIG. 8B shows the analysis of a second sample image 400C that has an even more subtle test line 351, which could be the result of slightly different lighting, contrast or focus, for example, when taking the second sample image 400C. Analytics are performed on the second test window 500C, extracted from the second sample image 400C, as shown in the second test-line probability chart 520C. Though the plots of the control line 353 are more or less the same as in the first test line probability chart 520B, the plots around the test line 351 are more subtle than in the first test line probability chart 520B.

FIG. 8C shows the analysis of a third sample image 400D that has no detectable test line 351. Analytics are performed on the third test window 500D, which is extracted from the third sample image 400C, as shown by the third test-line probability chart 520D. The plots of the control line 353, once again, are more or less the same as in the first and second test line probability charts 520B and 520C. The plots around the test line region 350 show no discernible test line.

Armed with the data from all three different test line probability plots 520B, 520C and 520D, statistical analytics can be used to determine the presence of a test line based 351, step 608. In one embodiment, a number of different criteria can be used to rate the statistical likelihood of a test line in the probability plots 520B, 520C and 520D. Whatever method is used to evaluate the presence of a test line 351, the analytics can be done in a matter of seconds, and the results sent back to the cell phone 100, or other computing device, step 610.

Figure 10:
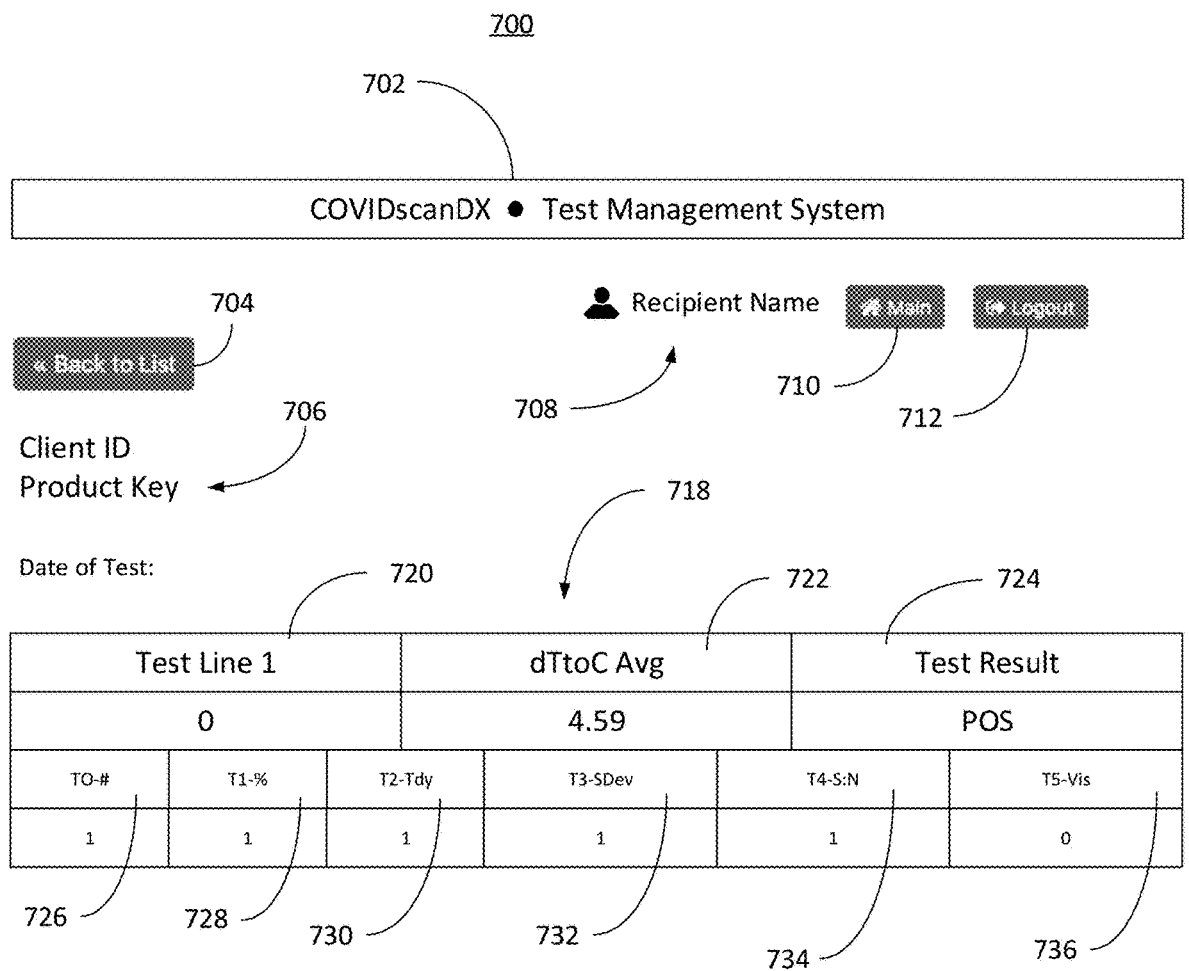
FIG. 10 illustratively depicts an administrator panel that can be accessed in the database reporting the results of a series of sample images consistent with embodiments of the present invention.
Figure 11:
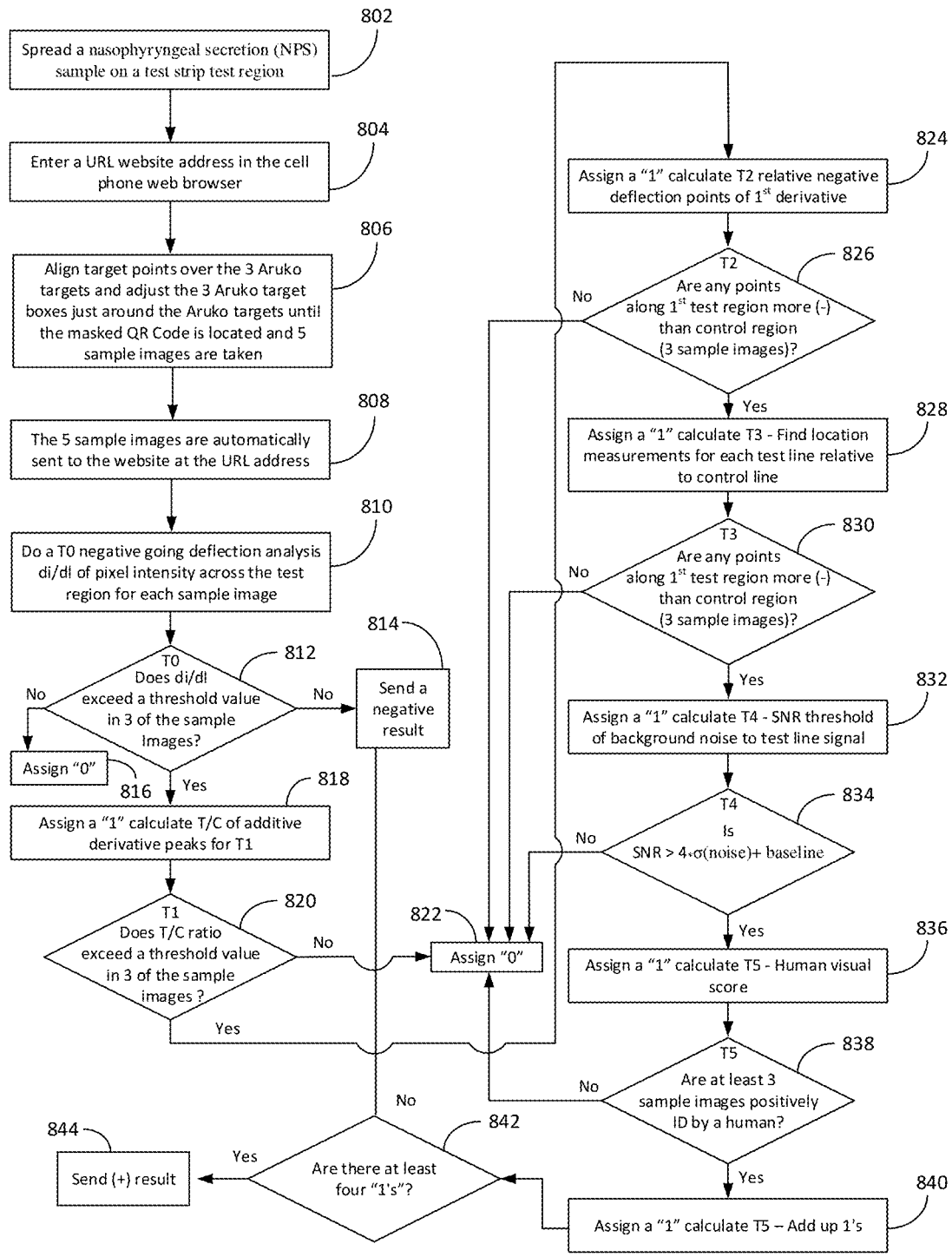
FIG. 11 is a block diagram of a method embodiment for evaluating a test line consistent with embodiments of the present invention.

FIG. 10 illustratively depicts an administrator panel that utilizes a method to detect a positive result at the limit of a detectable test line consistent with embodiments of the present invention. That administrator panel 700 can be accessed in the database reporting the results of a series of sample images 400. As shown, the administrative panel layout 700 is for a COVIDscanDX test 702, which shows the recipients name 708 with tabs that can be toggled by an end-user to go to the main screen 710 to logout 712 or go back to the list of data tests 704. There is also an area for client identification, product key and date of test 706. The results section 718 shows Test Line 1 720 (which is 0), derivative value of Test to Control Average 722 (which is 4.59) and the Test Result 724 (which is positive). Under these are the six threshold values 726-736 together establish either a positive or negative test result. Typical lateral flow test readers on the market today, which use similar technology to the lateral flow test strip 210, evaluate test line intensity (of the test line 351) by itself using visual or fluorescent illumination. In some cases the test line 351 is measured against the control line 353 simply using a Test-line over control-line (T/C) intensity ratio.

One embodiment for a method to evaluate a test line utilizes five sample images 400 to determine the presence of a test line 351, which if found is indicative of a positive test. After receiving a test card 200 and test strip 210, an end-user will collect and NPS sample 363 by swabbing their nose and mouth applying the collected NPS sample 363 (generally in a sample solution mixture 370) over the test region 350, step 802. After waiting 30 minutes and after a red control line 353 appears, the end-user will go to a web browser on their cell phone 100 and enter in the URL website address provided on the test card 200, step 804. The end-user will then position the rare cell phone camera 102 over the test card front surface 202 aligning the three target points over the Aruco targets 233, 234 and 235 until three Aruco target boxes 420 lock on to the Aruco targets 233, 234 and 235. When the cell phone position is adjusted and the three Aruco targets 233, 234 and 235 are just inside of the three Aruco target boxes 420, a QR box 422 will appear around the masked QR code 315 and take five focused with high contrast (near optimized) pictures 400, step 806. The sample pictures 400 will be taken automatically as soon as the obscured QR code 315 is able to be photographed ensuring high fidelity. The five sample pictures 400 are automatically sent to the database 130 behind the URL, step 808. Once in the database 130, analytics to evaluate the presence of a positive test line 351 can commence.

The method to evaluate the test line is well suited detect a test line signal 351 at the limits of what can be detected. Six threshold variables, T0-T5 726-736, describe different aspects of the signal that when combined are used to ascertain a positive or negative test result. Each of the threshold variables 726-736 is assigned either a 0 or 1 corresponding to a particular criteria that is either false or true, respectively.

The first criteria, T0 726 (step 810), is a slope change derivative evaluation metric indicating any light to dark pixel change across the test line region 350. More specifically a negative trending deflection in the first derivative of the normalized line profile 562 di/dl (di =instantaneous change of intensity, dl=corresponding instantaneous length, or position, at di) is depicted by the differential curve 564, of FIG. 8A. As shown in the decision block 812, if the value of di/dl meets or exceeds a threshold value in 3 or more of the sample images 400, then assign "1" to T0 726 (FIG. 10) and proceed to the next criteria, T1 728 step 818. If the value of di/dl does not meet or exceed the threshold value in 3 or more of the sample images 400, then assign "0" to T0 726 and send a negative result to the end-user, via their phone for example, step 814 (the test evaluation is over).

The second criteria, T1 728 (step 818), is a test line 351 to control line 353 ratio (T/C) of the a maximum amplitude of the absolute value of the negative sloped first derivative peak summed with the positive sloped first derivative peak value in both the test line 351 and control line 353. This is graphically shown by the "▲" of FIG. 8A. As shown in decision block 820, if the T/C ratio is greater than a T/C threshold number in at least 3 of the samples then assign a "1" to T1 728 and go to the third criteria, T2 730 (step 824), otherwise it enter in a "0" in T1 728, step 822.

The third criteria, T2 730 (step 824), is the absolute magnitude of the negative deflection in the first derivative of the test line 351. As shown in decision step 826, if the test region 350 possesses a negative deflection in the first derivative that is more negative than the negative deflection in the first derivative of the control region 352, then T2 730 is a "F" proceed to step 828, otherwise enter in a "0" at T2 730, step 822.

The fourth criteria, T3 732 (step 828), evaluates for jitter to assess how much a person might be wiggling their cell phone while taking a picture. Jitter can be determined through location measurements of where the test line 351 is relative to the control line 353. With respect to FIG. 8A, a location measurement is the distance between the negative peaks in the test region 350 and in the control region 352 along the first derivative line (see the upper "▲" in each predicted line 351 and 353) Likewise, this can be accomplished by taking the distance between the positive peaks in the test region 350 and control region 352 along the first derivative line (see the lower "▲" in each predicted line 351 and 353). Optionally, the two positive peaks and the two negative peaks can be combined to get a more robust mathematical value. Standard deviation (σ) can be determined from the 5 sample images 400 taken. As shown in the decision step 830, if the standard deviation is less than 1.5 for at least 3 sample images 400 then T3 732 is a "1" go to step 832, otherwise T3 732 is a "0", step 822.

The fifth criteria, T4 734 (step 832), is a signal-to-noise (SNR) ratio of a possible test line 351 versus the background noise. This can be accomplished by calculating the standard deviation (σ) of the background noise 517 between the test line region 350 and the control line region 352 for each sample image 400 based on values obtained from the first derivative curve between the regions 350 and 352. Next, the mean, or optionally the median, of the background noise is calculated to establish an offset. As shown in step 838, if 4* σ (background noise)+offset is smaller than the signal in the test line region 351, then the images score a "1" at T4 734 and go to step 840, otherwise T4 734 is a "0", go to step 822.

The signal in the test region can be established by the peak derivative signal (see the upper "▲"), or the difference between the positive and negative peak derivative signals.

The sixth criteria, T6 736 (step 836), is a human visual score where a human evaluates a line or no line. As shown in decision step 838, if at least 3 sample images are visibly seen then T5 736 is a "1" and go to step 840, otherwise T5 736 is a "0", go to step 822.

The results ("1's" and "0's") are added up to assess the likelihood of a positive test line 31, step 840. The result is considered positive if at least 4 criteria out of the 6 criteria are a "1", decision step 842. Accordingly, if this is the case then a positive result is sent back to the end-user, step 844. If this is not the case in a negative result is sent back to an end-user, block 814. Certain embodiments envision weighting certain criteria over others based on accumulating large statistical data (a learning/evolving algorithm). Other embodiments envision adding criteria, subtracting criteria or changing criteria as more information is gathered. Assigning points "1" and "0" is one method to evaluate a test line 351 if the majority of the signals show 'something discernible' in the test line region 350.

With the present description in mind, below are some examples of certain embodiments illustratively complementing some of the methods and apparatus embodiments to aid the reader. The elements called out below in view of the various figures are examples provided to assist in the understanding of the present invention and should not be considered limiting.

In that light, certain embodiment contemplate a biological sensitivity test strip method comprising: providing a test strip 210 possessing a test line region 350, a template 202 adjoining/accompanying the test strip 210, a QR code 300 visibly disposed on the template 202; exposing the test line region 350 to an activation agent 363, such as a pathogen; after the exposing step, focusing a digital camera 102 on the QR code 300, the digital camera 102 linked to a computer 128 that includes a microprocessor 120 and non-transient memory 122; partially obscuring the QR code 300 with a contrast reducing mask 310 generated by a QR code obscuring algorithm 123 executed by the microprocessor 120, the QR code obscuring algorithm 123 reducing functionality of a QR code capturing algorithm 125 also executed by the microprocessor 120; and capturing at least one image 400 of the test line region 350 after the exposing step while the QR code 300 is being partially obscured 315.

The biological sensitivity test strip method embodiment further comprising increasing time for the QR code capturing algorithm required to capture an image of the obscured QR code 315. Increasing the time in one example is to increase the average time it takes for a QR code algorithm to adequately capture an image of the QR code. For example, if on average it takes 1 second to capture or otherwise identify a QR code that is not obscured in any way, the obscured QR code may now take 2 seconds on average to be captured.

The biological sensitivity test strip method of claim embodiment further contemplating wherein the mask 310 has a mask color and the test line 351 has a test line color, the mask color and the test line color are essentially the same.

The biological sensitivity test strip method embodiment further envisioning wherein the mask 310 is less than or equal to the size of the QR code 300.

The biological sensitivity test strip method embodiment further imagining wherein the camera 102, computer 128, microprocessor 120 and non-transitory memory 122 are comprised by a smart phone 100 or tablet.

The biological sensitivity test strip method embodiment further comprising identifying a test line 351 in the test line location 350. Yet the method can further comprise reporting to a central database a positive test for the test strip 210.

The biological sensitivity test strip method embodiment further comprising capturing an image 400B having an image perimeter 402 defined as containing three Aruco squares and the QR code 300. This embodiment further envisioning sending the image perimeter 402 to a server system 130.

The biological sensitivity test strip method embodiment further comprising windowing the test line region 350 and a control line region 354 within an evaluation test window 500, the evaluation test window 500 extending distally 506 from both the control line region 354 and the test line region 354, the test line region includes the control line 353. This can further comprise evaluating the test line region 350 for a test line 351 using integration and/or derivation of any change in pigmentation along the evaluation test window 500. Optionally this can further comprise wherein the evaluating step is accomplished in a server system 130 that is remote to the computer 128 or further comprise sending at least the evaluation test window 500 to a server system 130. Other embodiments envision this method wherein the test window 500 is defined by a positioning of three Aruco squares on the template 202.

The biological sensitivity test strip method embodiment further considering wherein a cellular phone comprises the digital camera 102, the microprocessor 120 and the non-transitory memory 122.

Yet other embodiments envision a test strip evaluation method comprising: providing a smart phone 100 that includes a digital camera 102, a QR code identification algorithm 125, and a QR code obscuring mask 310; locating a QR code 300 with the camera 102; creating an obscured QR code 315 by masking the QR code 300 with the QR code obscuring mask 310; focusing the camera 102 on the obscured QR code 315 by way of or otherwise as controlled by the QR code identification algorithm 125 (the QR code algorithm 125 controls the camera focus to capture the QR code 300); and taking a photograph with the digital camera 102 of the obscured QR code 315 and an unobstructed region 405 extending beyond the obscured QR code 315.

The test strip evaluation method embodiment further comprising an evaluation test window 500 that includes a control line 353 and a test line region 350 that has been exposed to an activation agent 363, the evaluation test window 500 is in the unobscured region 405. This embodiment can further comprise evaluating the test line region 350 for a test line 351 using integration and/or derivation of pigmentation along the evaluation test window 500.

The test strip evaluation method embodiment further envisioning wherein the obscured QR code 315 forces the camera 102 to better focus on the QR code 300 and the unobscured region 405.

While still other embodiments contemplate a mobile touchscreen computing device 100 comprising: a touchscreen 112; a digital camera 102; non-transitory memory 122; a computer processor 120; a QR code detection algorithm 125 that locates a QR code 300 displayed on a planar surface, focuses the digital camera 102 on the QR code 300, acquires an image of the QR code 300 with at least a region 405 extending beyond the QR code 300 with the digital camera 102, the region 405 including a biologically activated test line region 350; a QR code obscuring algorithm that partially inhibits (masks) only the QR code 300 but not the region 405 to the QR code detection algorithm 125, the QR code obscuring algorithm reduces efficacy of the QR code detection algorithm 125.

The above sample embodiments should not be considered limiting to the scope of the invention whatsoever because many more embodiments and variations of embodiments are easily conceived within the teachings, scope and spirit of the instant specification.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, though a cell phone is primarily used herein as an example other kinds of computing devices including a tablet, a personal digital assistant, or other device comprising a camera can be equally used without departing from the scope and spirit of the present invention. The while maintaining the core functionality, for example. Another example is though the test strip is directed to a Covid 19 test strip, other biological or chemical test strips can be equally used without departing from the scope and spirit of the present invention. In another example a QR code is used however other two-dimensional decals, barcodes, or other indicia can be equally used while still maintaining substantially the same functionality without departing from the scope and spirit of the present invention. Further, the term "one" is synonymous with "a", which may be a first of a plurality.

It will be clear that the present invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the invention disclosed and as defined in the appended claims.

What is claimed is:

1. A biological sensitivity test strip method comprising:
   providing a test strip possessing a test line region, a template accompanying the test strip, and a QR code visibly disposed on the template;
   exposing the test line region to an activation agent;
   after the exposing step, focusing a digital camera on the QR code, the digital camera linked to a computer that includes a microprocessor and non-transient memory;
   partially obscuring the QR code with a contrast reducing mask generated by a QR code obscuring algorithm executed by the microprocessor, the QR code obscuring algorithm reducing functionality of a QR code capturing algorithm that is also executed by the microprocessor; and
   capturing at least one image of the test line region after the exposing step while the QR code is being partially obscured.

2. The biological sensitivity test strip method of claim 1 further comprising increasing an average time for the QR code capturing algorithm required to capture an image of the obscured QR code.

3. The biological sensitivity test strip method of claim 1, wherein the mask has a mask color and the test line has a test line color, the mask color and the test line color are essentially the same.

4. The biological sensitivity test strip method of claim 1, wherein the mask is less than or equal to the size of the QR code.

5. The biological sensitivity test strip method of claim 1, wherein a smart phone or tablet comprise the camera, computer, microprocessor and non-transitory memory.

6. The biological sensitivity test strip method of claim 1 further comprising identifying a test line in the test line location.

7. The biological sensitivity test strip method of claim 6 further comprising reporting to a central database a positive test for the test strip.

8. The biological sensitivity test strip method of claim 1 further comprising capturing an image having an image perimeter defined as containing three Aruko squares and the QR code.

9. The biological sensitivity test strip method of claim 8 further comprising sending the image perimeter to a server system.

10. The biological sensitivity test strip method of claim 1 further comprising windowing the test line region and a control line region within an evaluation test window, the evaluation test window extending distally from both the control line region and the test line region, the test line region includes the control line.

11. The biological sensitivity test strip method of claim 10 further comprising evaluating the test line region for a test line using integration and/or derivation of any change in pigmentation along the evaluation test window.

12. The biological sensitivity test strip method of claim 10, wherein the evaluating step is accomplished in a server system that is remote to the computer.

13. The biological sensitivity test strip method of claim 10 further comprising sending at least the evaluation test window to a server system.

14. The biological sensitivity test strip method of claim 10 further comprising defining the test window by positioning three Aruko squares on the template.

15. The biological sensitivity test strip method of claim 1, wherein a cellular phone comprises the digital camera, the microprocessor and the non-transitory memory.

16. A test strip evaluation method comprising:
    providing a smart phone that includes a digital camera, a QR code identification algorithm, and a QR code obscuring mask;
    locating a QR code with the camera;
    creating an obscured QR code by masking the QR code with the QR code obscuring mask;
    focusing the camera on the obscured QR code, the camera being controlled by the QR code identification algorithm; and
    taking a photograph, with the digital camera, of the obscured QR code and an unobstructed region extending beyond the obscured QR code.

17. The test strip evaluation method of claim 16 further comprising an evaluation test window that includes a control line and a test line region that has been exposed to an activation agent, the evaluation test window is in the unobscured region.

18. The test strip evaluation method of claim 17 further comprising evaluating the test line region for a test line using integration and/or derivation of pigmentation along the evaluation test window.

19. The test strip evaluation method of claim 16, wherein the obscured QR code forces the camera to better focus on the QR code and the unobscured region compared to focusing on an unobscured QR code.

20. A mobile touchscreen computing device comprising:
a touchscreen;
a digital camera;
non-transitory memory;
a computer processor;
a QR code detection algorithm that locates a QR code displayed on a planar surface, that focuses the digital camera on the QR code, and that acquires an image of the QR code with at least a region extending beyond the QR code with the digital camera,
the region including a biologically activated test line region;
a QR code obscuring algorithm that partially inhibits (masks) only the QR code but not the region to the QR code detection algorithm, the QR code obscuring algorithm reduces efficacy of the QR code detection algorithm.

* * * * *